United States Patent [19]

Bird

[11] 4,037,994
[45] July 26, 1977

[54] PRESSURE UNLOADING VALVE DEVICE FOR COMPRESSOR

[76] Inventor: Forrest M. Bird, 212 NW. Cerritors, Palm Springs, Calif. 92262

[21] Appl. No.: 563,692

[22] Filed: Mar. 31, 1975

[51] Int. Cl.² ............................................. F04B 49/02
[52] U.S. Cl. ................................ 417/316; 128/142.3; 128/145.6; 200/61.86; 251/191; 417/440
[58] Field of Search .................... 417/299, 26, 33, 440, 417/442, 563, 298, 306, 557, 316; 128/145.6, 203, 145.5, 145.8, 142.3, DIG. 17; 200/61.86, 83 Q; 251/191

[56] References Cited
U.S. PATENT DOCUMENTS

| | | | |
|---|---|---|---|
| 1,888,542 | 11/1932 | Rosberg | 417/440 X |
| 1,942,433 | 1/1934 | Lindsay | 417/316 |
| 2,083,740 | 6/1937 | Paullin, Jr. | 417/316 |
| 2,434,771 | 1/1948 | Mueller et al. | 417/316 X |
| 2,925,246 | 2/1960 | Sardeson | 251/191 |
| 3,095,904 | 7/1963 | Thaning | 251/191 X |
| 3,515,135 | 6/1970 | Flower et al. | 128/145.6 |
| 3,700,002 | 10/1972 | Christie | 200/61.86 X |
| 3,788,769 | 1/1974 | Glass et al. | 417/26 |
| 3,827,827 | 8/1974 | Hill | 417/299 X |
| 3,885,739 | 5/1975 | Tuttle | 417/33 X |

FOREIGN PATENT DOCUMENTS 759,668  10/1956  United Kingdom .................. 251/191

Primary Examiner—John J. Vrablik
Assistant Examiner—Edward Look
Attorney, Agent, or Firm—Flehr, Hohbach, Test, Albritton & Herbert

[57] ABSTRACT

A valve device is disclosed for unloading pressure from a compressor of the type utilized in a medical respirator. The device is formed with a cylindrical chamber containing a compressible elastomeric member. Inlet and relief ports of the valve open into the chamber, and the inlet port is connected with the outlet of the gas compressor. Bistable actuator means is provided for moving a plunger within the chamber which in turn causes the cylindrical member to assume either a compressed or uncompressed state. In its uncompressed state a radial clearance between the outer wall of the elastomeric member and the chamber provides a flow path between the inlet and relief ports to bleed pressure from the compressor. In its compressed state the elastomeric member expands to occlude the flowpath and prevent pressure bleed-off from the compressor. A switch is provided to open and close a circuit between the compressor and a source of electrical power responsive respectively to the uncompressed and compressed states of the elastomeric member.

4 Claims, 4 Drawing Figures

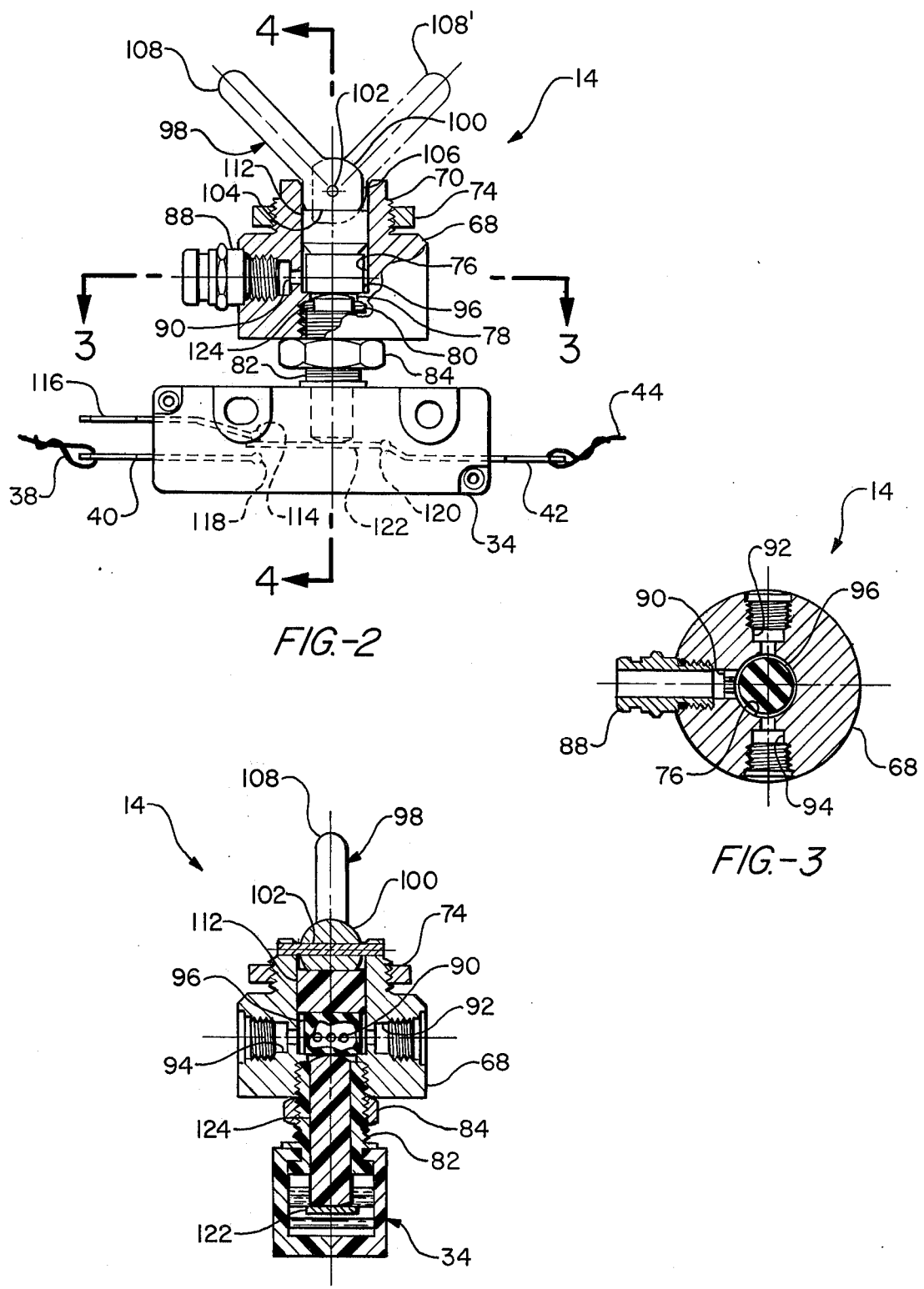

PRESSURE UNLOADING VALVE DEVICE FOR COMPRESSOR

BACKGROUND OF THE INVENTION

This invention relates in general to gas compressors and in particular to an unloading valve device for use with gas compressors of the type used for driving medical respirators. A critical problem in gas compressors is the requirement of unloading trapped or deadhead pressure from the working chamber or cylinder head when the compressor is shut down so that it can be more easily restarted at a later time. In many cases the deadhead pressure which is developed upon shutdown is of such magnitude that it becomes extremely difficult or even impossible to restart the compressor unless the deadhead pressure is relieved. This condition particularly occurs when a compressor is stopped at a point in its cycle where the piston or diaphram is approaching its top dead center position. Where the compressor is electrically driven, a serious thermal overload in the motor can occur if the deadhead pressure is not relieved.

Heretofore various devices have been employed in an attempt to relieve the deadhead pressure from compressors. Among these devices are unloading valves such as whisker valves or centrifugal switches which are arranged to bleed pressure from the compressor's working chamber upon shutdown. However, such prior devices are relatively complex and expensive in design and construction, and have not been completely satisfactory in operation. A need has therefore been recognized for an improved means for unloading deadhead pressure from compressors.

OBJECTS AND SUMMARY OF INVENTION

It is a general object of the invention to provide a new and improved device for unloading deadhead pressure from a gas compressor.

Another object is to provide an unloading valve device which will automatically relieve deadhead pressure from a compressor upon shutdown.

Another object is to provide an unloading valve device of the type described which is less expensive and complex in design and construction as compared with existing designs and which will operate with a high degree of reliability.

Another object is to provide an unloading valve device of the type described in which operation of a single control element serves to either open or close a pressure bleed-off path from the compressor while respectively opening or closing a circuit supplying the electrical power which operates the compressor.

Another object is to provide an unloading valve device of the type described in which a resilient disk is operated between compressed and uncompressed states within a chamber such that elastic expansion of the disk when it is compressed shuts off a gas bleed path from the compressor and at the same time serves to close switch contacts in a circuit directing electric power to operate the compressor.

The invention in summary includes a valve body which forms a cylindrical chamber having inlet and relief ports. The inlet port is connected through a hose with the outlet of a gas compressor. An elastomeric disk is contained within the chamber and the disk is sized with a radical clearance from the walls of the chamber which forms a gas relief flow path between the inlet and the relief ports. Bistable valve actuator means is provided and includes a double lobe cam which operates to move a plunger for causing the disk to assume compressed and uncompressed states. In the compressed state the disk expands laterally into an oblate shape in contact with the chamber wall to occlude the gas relief flow path, and at the same time a portion of the disk bulges through a circular opening in the chamber and actuates another plunger to close contacts in a circuit which connects a source of electrical power to the compressor motor. In the uncompressed state of the disk the contacts are opened to de-energize the motor and at the same time open the relief flow path to bleed gas from the compressor for eliminating deadhead pressure.

The foregoing and additional objects and features of the invention will become apparent from the following description in which the preferred embodiments have been set forth in detail in conjunction with the accompanying drawings.

BRIEF DESCRIPTION OF THE DRAWINGS

FIG. 2 is a side elevation view to a greatly enlarged scale of an unloading valve device which is a component of the apparatus of FIG. 1;

FIG. 3 is a cross sectional view taken along the line 3—3 FIG. 2;

FIG. 4 is an axial section view taken along the line 4—4 of FIG. 2.

DESCRIPTION OF THE PREFERRED EMBODIMENT

Figure 1:
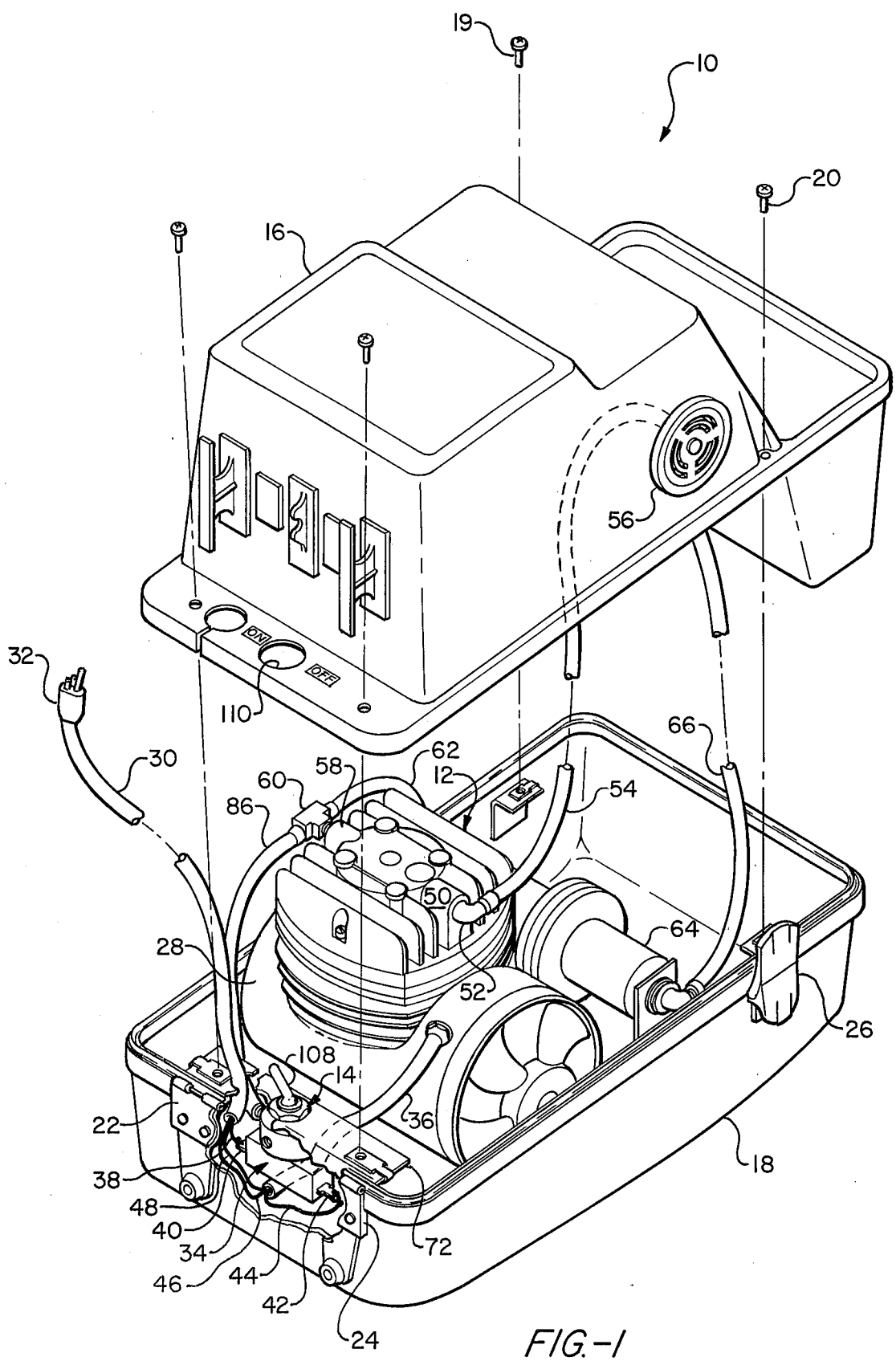
FIG. 1 is perspective partially exploded view of apparatus incorporating one embodiment of the invention.

In the drawings FIG. 1 illustrates generally at 10 medical respirator apparatus which incorporates an air compressor 12 together with an unloading valve device 14 made in accordance with the invention. While the invention herein will be described in relation to a medical respirator it is understood that the invention will find application in many other systems or apparatus employing a gas or air compressor.

Respirator unit 10 is of portable construction and includes upper and lower housing shells 16, 18 which are adapted to fit together to form a closed chamber. The two shells are secured together by means of four screws 19, 20. A suitable dome-shaped cover, not shown, may be pivotally mounted at one end of the lower shell by hinge joints 22, 24, and a suitable snap action latch 26 is mounted on the side of the lower shell for releasably locking with the cover.

Air compressor 12 is mounted within lower shell 18 and preferably comprises a diaphragm type compressor driven by an electric motor within casing 28. In use with the respirator unit the compressor is adapted to supply an output pressure on the order of 50 psi which drives a suitable respirator apparatus, not shown, mounted within the upper shell. The compressor could also be of a reciprocating piston design, depending upon the specification and requirements of the particular application.

The motor of compressor 12 is powered from a suitable 110 VAC power source by means of a power cable 30 connected through plug 32 with a suitable power receptacle. The conductor wires of cable 30 are connected through microswitch 34 of relief valve unit 14 and a cable 36 leads into casing 28 to the compressor motor. A power wire 38 is connected with one terminal 40 of the microswitch and the opposite terminal 42 is connected with a wire 44 leading to the compressor motor. Another power wire 46 runs directly to the motor while a third wire 48 provides a ground connection for the motor.

An intake port 50 of the compressor head is connected through an E1 fitting 52 and flexible hose 54 with a suitable intake filter 56 which is mounted on and opens through the side of top shell 16. An outlet port 58 of the compressor head is connected through one side of a Tee fitting 60 with a flexible hose 62 leading to a suitable plenum reservoir or accumulator 64. The accumulator is in turn connected through a flexible hose 66 with the respirator apparatus mounted in the upper shell. An outlet hose, not shown, from the respirator apparatus leads through an opening on the opposite side of the upper shell to a suitable patient adapter, such as a mouthpiece or face mask for supplying gas to the patient's airway.

Referring to FIGS. 2-4, unloading valve device 14 includes a valve body 68 formed of a suitable rigid material such as aluminum. The upper circular end 70 of the valve body is threaded for mounting onto a bracket 72 which is carried within one end of lower shell 18. A lock nut 74 is also mounted on the end of the valve body for locking the device 14 onto the bracket 72.

Valve body 68 is formed with a vertically extending cylindrical chamber 76 which opens upwardly through end 70. An intrusive circular shoulder 78 is formed about the lower end of chamber 76, and a tapped opening 80 is formed below shoulder 78 in axial alignment with the chamber. Microswitch 34 includes an upwardly extended threaded hollow stem 82 which engages into opening 80 of the valve body. Microswitch 34 and its stem are adapted to be screwed in and out of opening 80 to adjust the axial position of the microswitch with respect to the valve body and thereby selectively adjust the operating sensitivity of the microswitch. A lock nut 84 is mounted about the stem 82 for locking the microswitch against rotation with respect to the valve body.

Compressor outlet 58 is also connected through Tee 60 and a flexible hose 86 with an adapter fitting 88 which is threadably mounted in a side of valve body 68. The adapter fitting communicates with an inlet port 90 comprising one or more (shown as three) radially extending apertures which open through the sidewall of chamber 76. A pair of diametrically opposed relief ports 92, 94 are formed through the sidewalls of the chamber, each at a 90° orientation from inlet port 90.

A cylindrical compressible member or disk 96, which is formed of a suitable elastomeric material such as neoprene rubber, is mounted within chamber 76 with its lower peripheral margin supported above shoulder 78. The material of disk 96 is selected with a durometer hardness value such that the disk can change shape between the uncompressed state having the cylindrical shape illustrated in FIG. 2 and an axially compressed state wherein it radially expands or distends into a bulged or oblate shape. The plastic memory of the disk causes it to contract and assume its uncompressed state whereby the outer cylindrical surface of the disk is radially spaced from chamber wall 76 to form an annular gas relief flow path leading from inlet port 90 to the relief ports 92 and 94. In the compressed state the outer surface of the disk is forced into sealing contact with the chamber wall and covers the inlet and relief ports so as to close off or occlude the gas relief flow path. Disk 96 is actuated between its compressed and uncompressed states by means of a bistable two position actuator 98. Actuator 98 includes a cam 100 which is mounted for back-and-forth rotation about a pin 102 secured across the valve body at the upper end of the chamber 76. Cam 100 is formed with a pair of transversely flat lobes 104, 106 which are positioned at an orthogonal orientation. An elongate arm 108 is formed integrally with the cam and extends upwardly from the valve body where it projects through an opening 110, FIG. 1, formed in the rim of upper shell 16 where it is accessible for manual operation. The cam 100 and arm 108 are adapted for operation between a first or "compressor-off" position, illustrated in solid line in FIG. 2, and a second or "compressor-on" position, illustrated in broken line at 108'. A rigid cylindrical plunger 112 is slidably mounted within chamber 76 between the upper end of disk 96 and cam 100.

The cam lobes are sized and proportioned so that lobe 104 is at a shorter radius from the center of rotation of the cam than the radius of lobe 106. In the compressor-off position of the cam, lobe 104 is brought into register with the upper surface of plunger 112 so that the latter is free to move upwardly as disk 96 assumes its uncompressed state due to its plastic memory. When the cam arm is turned to the compressor on position at 108', lobe 106 is brought into register with the upper surface of the plunger which is thereby driven or cammed downwardly to exert a thrust force which causes disk 96 to assume its compressed state.

Microswitch 34 includes contact elements comprising a normally closed contact point 114 connected with a terminal 116, a normally open contact point 118 connected with terminal 40, and a common contact point 120 connected with terminal 42. A movable contact element 122 is connected at one end with contact point 120 and is yieldably biased upwardly as by spring action so that its distal end is against the normally closed contact point 114. A rigid cylindrical plunger 124 is slidably mounted within stem 82. The lower end of the plunger is in operating engagement with movable contact element 122, and the upper end of the plunger is juxtaposed below the lower surface of disk 96 adjacent shoulder 78. When the disk is operated into its compressed state, the lower disk portion bulges downwardly through the opening of shoulder 78 and exerts a downward thrust force against plunger 124, which is thereby driven downwardly to switch contact element 122 against normally open point 118. The power circuit is thereby closed to energize the compressor motor. With the disk in its uncompressed state, the thrust force on plunger 124 is released to permit element 122 of the microswitch to be moved away from contact 118 so that the circuit to the motor is opened.

In the use and operation of the invention, plug 32 of the power cable is first connected with the power supply receptacle. To energize the compressor for driving the respirator, arm 108 of the cam is manually switched to the on position 108', where it is retained due to the flat configuration of its lobe 106. At the same time plunger 112 is cammed down to exert a thrust force against disk 96 which elastically expands radially into contact with the wall of chamber 76 so that the flow path between the inlet and relief ports is occluded. The lower portion of the disk also bulges downly through the opening within shoulder 78 to exert a thrust force against microswitch plunger 124. This plunger is thereby driven downwardly to move contact element 122 against normally open contact 118. The power circuit is thus closed for operating the compressor motor. Air is inducted into the working chamber of the compressor through intake filter 56 and hose 54 and is discharged at substantially 50 psi through outlet port 58 into Tee 60. Because the relief flow path through the valve 14 is blocked, the flow from the compressor is directed through hose 62 into accumulator 64 and then through hose 66 to drive the respirator.

To shut off the compressor, cam arm 108 is moved to its off position so that the smaller radius lobe 104 is brought into register with plunger 112. The plastic memory of disk 96 is thus free to move plunger 112 upwardly as the disk assumes its uncompressed state. Displacement of the outer wall of the disk away from the chamber wall re-establishes communication between the inlet and relief ports. At the same time, the lower portion of the disk retracts from its bulged conditions to permit mircoswitch plunger 124 and contact element 122 to be urged upwardly and open the circuit to the compressor motor. When the compressor stops any deadhead pressure within its working chamber is free to bleed off through hose 96 and through the relief flow path of valve 14 for discharge into the atmosphere through relief ports 92, 94. During the following cycle of operation, compressor can be easily started through operation of cam arm 108 without the resistance which would otherwise occur from such deadhead pressure.

While the foregoing embodiments are at present considered to be preferred, it is understood that numerous variations and modifications may be made therein by those skilled in the art, and it is intended to cover in the appended claims all such variations and modifications as fall within the true spirit and scope of invention.

I claim:

1. A device for use with a gas compressor having an outlet passage for directing gas to end use apparatus, including the combination of a valve body having at least one relief port and an inlet port in connection with the outlet passage of said compressor, means forming a chamber in the valve body for establishing fluid communication with said inlet and relief ports, a compressible elastomeric member mounted within said chamber, said member being sized to define in its substantially uncompressed state a clearance with the wall of the chamber, said clearance establishing a gas relief flow path through the chamber between said inlet and relief ports, said member in its compressed state contacting said chamber wall to occlude said relief flow path, and actuator means operable in one mode for causing said member to assume its compressed state and occlude the flow path while energizing said compressor, said actuator means further being operable in another mode for causing said member to assume its uncompressed state while said compressor is deenergized whereby gas pressure is relieved from the compressor outlet through said relief flow path and through the relief port of the valve body, said actuator means including a plunger slidably mounted for movement within the chamber, cam means operable for movement between a compressor-on and a compressor-off position, said cam means in the compressor-on position moving the plunger in a first direction for exerting a thrust force against the elastomeric member to cause the same to assume its compressed state, the cam means in said compressor-off position permitting movement of the plunger in a second direction away from the elastomeric member to cause the same to assume its uncompressed state, electrical contact means operable between first and second positions in which said gas compressor is operatively disconnected and connected, respectively, with a source of electrical power, and a second plunger disposed in operating engagement with said contact means, said second plunger being positioned in juxtaposed relationship with said elastomeric member whereby the latter undergoes respective elastic bulging and contraction between said compressed and uncompressed states for moving the second plunger to operate said contact means between respective second and first positions.

2. Apparatus for unloading topped gas pressure from a compressor which is operated by a source of electrical power to supply gas under pressure through an outlet passage, the apparatus including the combination of a housing defining a cylindrical chamber, an inlet port in the housing connected with the outlet passage of the compressor for communicating gas therefrom into the chamber, a relief port in the housing for bleeding gas from the chamber, an elastomeric cylindrical disk mounted in the chamber, said disk being sized with a radial clearance from the cylindrical chamber, means forming a circular shoulder in one end of the chamber for supporting a peripheral end margin of the disk, a first plunger mounted for movement within the chamber on a side of the disk opposite said one end of the chamber, a cam rotatably mounted on the housing between first and second positions in operating contact with the first plunger, said cam in its second position urging the first plunger towards said one end of the chamber for compressing said disk whereby the outer surface thereof distends radially into sealing contact with the wall of the chamber for occluding communication between said inlet and relief port, said cam in its first position permitting movement of the first plunger in a direction away from said one end of the chamber whereby the outer surface of said disk is permitted to retract by the action of its plastic memory away from the wall of the chamber permitting fluid communication between said inlet and relief ports, means forming a circuit for connecting said source of electrical power with said compressor, said circuit means including electrical contact means operable between first and second positions for respectively opening and closing said circuit, and second plunger means operably connected with said contact means, said second plunger means having one end positioned in juxtaposed relationship with the disk whereby distension thereof responsive to movement of the first plunger as the cam is moved to said compressor-on position operates the contact means to said second position, and retraction of said disk responsive to movement of the first plunger as the cam is moved to said compressor-off position operates said contact means to said first position.

3. In a respirator unit for delivering a supply of gas to the airway of a patient, the combination of compressor means for discharging a supply of gas under pressure through an outlet, said compressor means being powered from a source of electrical energy, a valve body defining a cylindrical chamber, inlet port means formed in the valve body for communicating gas from the compressor outlet into the chamber, relief port means formed in the valve body for bleeding gas from the chamber, an elastomeric member mounted in the chamber, said member being sized and proportioned to assume an uncompressed state defining a radial clearance between the walls of the member and chamber and a compressed state in which the member radially distends into contact with the chamber walls for occluding flow through the chamber between the inlet and relief port means, bi-stable actuator means selectively operable between first and second positions in which said elastomeric member is respectively urged between its uncompressed and compressed states, and circuit means for opening and closing a conductive path between said source of electrical energy and said compressor when the elastomeric member is in its respective uncompressed and compressed states, the actuator means is mounted in one end of said chamber and includes an element which in said second position contacts the elastomeric member with a thrust force for causing the latter to assume its compressed state, said actuator means in its first position releases the element from the elastomeric member to permit the latter to assume its uncompressed state through the action of its plastic memory, and said valve body includes means forming a shoulder which surrounds a central opening at the opposite end of the chamber, said shoulder supporting the elastomeric member in an axial direction, sand said circuit means includes a switch operable between opened and closed modes, a plunger operably mounted with said switch, said plunger having one end extending into said valve body adjacent said central opening in juxtaposition with the elastomeric member whereby said member in its compressed state bulges through said central opening and exerts a thrust force againt said one end of the plunger for operating the switch to its closed mode.

4. A respirator unit as in claim 3 in which said element of the actuator means comprises an additional plunger mounted for axial sliding movement in said one end of the chamber operably mounted with the elastomeric member, together with a cam having first and second angularly disposed lobes, said first lobe having a cam lift which is greater than said second lobe, and means for selectively actuating the cam to a position at which the first lobe engages the additional plunger and moves the same towards the elastomeric member for compressing the latter, said last mentioned means further activating the cam to another position at which the second lobe permits movement of the additional plunger away from the elastomeric member to permit the same to assume its uncompressed state.

* * * * *